United States Patent [19]

Takagi

[11] Patent Number: 4,950,262

[45] Date of Patent: Aug. 21, 1990

[54] EXCRETION ABSORBING-AND-HOLDING DEVICE

[75] Inventor: Katsumasa Takagi, Yokohama, Japan

[73] Assignee: Koyo Disposable Goods Co., Ltd., Yokohama, Japan

[21] Appl. No.: 384,889

[22] Filed: Jul. 27, 1989

Related U.S. Application Data

[63] Continuation of Ser. No. 101,527, Sep. 29, 1987, abandoned.

[51] Int. Cl.[5] .......................................... A61F 13/16
[52] U.S. Cl. ................................. 604/385.1; 604/369; 604/378
[58] Field of Search ............... 604/347, 348, 354, 367, 604/369, 378, 380, 381, 385.1

[56] References Cited

U.S. PATENT DOCUMENTS

| | | | |
|---|---|---|---|
| 791,354 | 5/1905 | Merkley | 604/369 |
| 1,139,941 | 5/1915 | White | 604/348 |
| 2,043,325 | 6/1936 | Jackson, Jr. | 604/378 |
| 2,277,043 | 3/1942 | Cohn | 604/348 |
| 2,538,758 | 1/1951 | Bricmont | 604/347 |
| 2,566,451 | 9/1951 | Julien | 604/347 |
| 3,182,661 | 5/1965 | Ribeiro et al. | 604/347 |
| 3,306,966 | 2/1967 | Matejcek et al. | 604/369 |
| 3,375,827 | 4/1968 | Bletzinger et al. | 604/380 |
| 3,577,989 | 5/1971 | Anderson | 604/348 |
| 4,031,897 | 6/1977 | Graetz | 604/347 |
| 4,285,342 | 8/1981 | Mesek | 604/378 |
| 4,526,825 | 7/1985 | Whitehead | 604/381 |
| 4,622,036 | 11/1986 | Goodrum | 604/381 |
| 4,681,577 | 7/1987 | Stern et al. | 604/380 |
| 4,685,914 | 8/1987 | Holtman | 604/369 |
| 4,753,645 | 6/1988 | Johnson | 604/385.1 |
| 4,787,896 | 11/1988 | Houghton et al. | 604/385.1 |

FOREIGN PATENT DOCUMENTS

| | | | |
|---|---|---|---|
| 0732887 | 4/1966 | Canada | 604/378 |
| 3544816 | 6/1987 | Fed. Rep. of Germany | 604/385.1 |
| 0055632 | 9/1935 | Norway | 604/354 |
| 2148126 | 5/1985 | United Kingdom | 604/347 |

Primary Examiner—Stephen C. Pellegrino
Assistant Examiner—Sharon Rose
Attorney, Agent, or Firm—Cushman, Darby & Cushman

[57] ABSTRACT

A device for the collection of bodily excretion having an expandable storage member in the form of bellows. The bellows having a minimum size prior to excretion, but increase in volume with the increase of waste liquid or solid passed from the body, thereby assuring that such waste liquid or solid is contained in the expandable storage without leakage no matter how much excretion may be discharged. The device has a guide strip for directing the flow of the excretion toward the expandable storage member at its rear part. The guide strip is made of a mass of spongy material compressed in the form of a thin sheet. It is effective to absorb and collect the excretion quickly by enlarging and restoring to its initial stress-free volume.

10 Claims, 8 Drawing Sheets

EXCRETION ABSORBING-AND-HOLDING DEVICE

This is a continuation of Application No. 07/101,527filed 09/28/87, now abandoned.

BACKGROUND OF THE INVENTION

The present invention relates to a device for absorbing and storing liquid and solid waste matter passed from the body, and more particularly to a device for absorbing and storing urine, faeces or monthly bleeding excreted from a bedridden person or patient.

As is well known, disposable paper diapers have been widely used by bedridden persons to collect bodily excretion for eventual disposal. These disposable diapers, however, have some defects. For instance, they are unusually large and unpleasing in appearance around the buttocks. The care required for the storage and transportation, and disposal after use is difficult. The application and removal from a bedridden person or patient is complicated. Finally the diaper has an unpleasant feeling when wet with urine.

In an attempt to reduce such disadvantages a urine or monthly bleeding absorber was proposed. It is composed of a surface sheet and a foam back laid on each other and sealed along their peripheries to provide a liquid absorbing-and-storing space therebetween. The absorber is small in size, and is like a bicycle saddle in shape.

Such a bicycle saddle-shaped urine absorber is free of the defects mentioned above. It also has a good fit, is easy to apply, has a reduced size, and a pleasing feeling and appearance when attached to the body. These advantages result from contouring the urine absorber so that the portion of the absorber near the crotch area of a wearer is thinner than the portion facing the bottom of a wearer, thereby permitting comfortable and easy leg movement of a patient. The absorber, however, has a reduced storage capacity because of its reduced size. The quantity of urine varies individually, ranging from 300 cc to 500 cc. A bicycle saddle-shaped urine absorber cannot cover such a relatively wide range of urine volume without an increase in size. In addition, sometimes it cannot hold the whole quantity of urine excreted thereby allowing urine leakage.

SUMMARY OF THE INVENTION

The main object of the present invention is to provide a device for collecting bodily excretion which is small, and is adapted to fit the urinary organ or anus comfortably, and is capable of enlarging its capacity enough to absorb and hold the whole amount of excretion, such as urine, feces or monthly bleeding without allowing the excretion to leak. Specifically, the device for collection of bodily excretion remains small until excretion, and in response to excretion its volume expands enough to absorb and hold the whole amount of excretion.

The device has a bicycle saddle shape and consequently has a small area which barely covers the urinary organ or anus. In this connection, it is necessary to permit excretion to spread in the absorbent material as quickly as possible because otherwise, excretion would leak from the absorber. In an attempt to make it possible to quickly absorb excretion in the absorbent materials, a guide strip which is made of the same material as the absorbent material, such as paper or ground pulp, is used for directing the flow of excretion towards the absorbent material. This is effective to prevent any leakage of excretion from the absorbing device to some extent, but those skilled in the art would realize that a thin, flat strip of paper or ground pulp cannot perfectly prevent leakage. Satisfactory results, in fact, could not be attained without meeting the following requirements: (1) quick collection of the urine excreted from the urinary organ no matter what position a bedridden person may take particularly in the case of incontinence; (2) quick transportation of excretion from a urine collecting place to a urine absorbing-and-storing place, that is, quick permeation; (3) ability for repeated collection, absorption and storage of excretion; (4) a guide strip which does cause a patient to feel uncomfortable when he wears the device, and (5) a reduction in size and thickness, while maintaining the capability to collect and store a maximum amount of excretion.

Accordingly, another object of the present invention is to provide an excretion absorbing-and-holding device which is small in size, and can effect (1) quick collection of the urine excreted from the urinary organ; (2) quick transportation of excretion from a urine collecting place to a urine absorbing-and-storing place; (3) repeated collection, absorption and storage of excretion after the guide strip and absorbent material once used has become dry by bodily temperature; (4) soft touch to the body; and (5) enlargement to a volume large enough to collect and store a possible maximum amount of excretion.

Still another object of the present invention is to provide an excretion absorbing-and-holding device which is small and light, and is easy to manufacture and use.

These and other objects are achieved by a device for collection of bodily excretion which comprises a flat surface member, a liquid-impermeable, flexible covering member of high-molecular weight material disposed on the flat surface member. The flat surface member and the flexible covering member are sealed so as to be liquid-tight along their periphery. A mass of absorbent material such as paper, ground pulp, high-molecular weight material and the like, is disposed in the space between the flat surface member and the covering member. The device further comprises expandable bellows integrally connected to the rear part of the covering member. The bellows are capable of increasing in volume with the increase of excretion.

In another embodiment, the device for the collection of bodily excretion comprises a flat surface member, a liquid-impermeable, flexible covering member of high-molecular weight material disposed on the flat surface member. The flat surface member and the flexible covering member are sealed liquid-tight along their peripheries. A mass of absorbent material such as paper, ground pulp, high-molecular weight material and the like is disposed in the space between the surface and covering members. The device further comprises expandable bellows integrally connected to the rear part of the covering member. The bellows are capable of increasing their volume with the increase of absorption of excretion. The device still further comprises a guide strip of pulp sponge material for directing the flow of excretion to the absorbent material. The guide strip is formed of pulp sponge and is prepared by mixing viscose, reinforcement fibre and bubble-forming crystal together; solidifying the mixture; and compressing the resultant spongy material into a thin sheet.

In use, the device for the collection of bodily excretion of the present invention is applied to the urinary organ, causing no unpleasant touch to the body. Prior to excretion the device remains small, with its bellows contracted. At the time of excretion the urine spreads in the mass of absorbent material until it has been saturated with urine, and then the urine reaches the entrance of the bellows. The bellows expand with the increase of the urine so that the whole amount of the urine may be held in the expanding space of the bellows, not allowing the urine to leak from the device. As is readily understood from the above, the device for collection of bodily excretion according to the present invention is small in size, thereby facilitating the attachment to the body adjacent the urinary organ or anus. The device can increase its storing space with the increase of excretion, thereby guaranteeing that the device is free of leakage of excretion. A longitudinal guide strip of compressed pulp sponge extends from the front part of the device facing the urinary organ towards the rear part of the device equipped with the bellows may be provided. When the urine passes from the body, it will be quickly absorbed in the guide strip after passing through the overlying surface member. Then, the guide strip will be saturated with urine so that the guide strip may return to its initial, pre-compression volume. Accordingly, a great amount of urine may be absorbed and held in the guide strip. As for the flow of the urine in the guide strip the waste liquid will spread in the thickness of the sponge-like structure under the influence of capillary attraction, and therefore it can spread quickly. While absorbing the urine, the guide strip will restore to its initial, stress-free volume, accordingly soaking up any additional quantity of waste liquid passed from the body. Then, the urine is transported to the absorbent material lying under the guide strip.

As seen from the above, the guide strip lying under the surface sheet member causes quick collection and transportation of the urine by absorbing the urine in the pulp sponge, expanding from its compressed minimum volume towards its initial, stress-free maximum volume. When the guide strip dries up because of bodily temperature, it can be soaked by urine again. The urine travels along the guide strip to reach the bellows. The bellows expands in volume to the extent that it may hold the urine without leakage. Thus, quick collection and storage of excretion can be effected without fail, no matter how much urine may be discharged.

DETAILED DESCRIPTION OF THE PREFERRED EMBODIMENT

Referring to the drawings, a device for the collection of bodily excretion wherein like numbers represent like parts throughout is indicated at "A", and is shaped like a bicycle saddle in plane view. It is composed of a flat surface member 2, a liquid-impermeable, flexible covering 3 of high-molecular weight material laid on the flat surface member 2 and sealed together along their periphery 5 by heat, and a mass of absorbent material such as paper or ground pulp 1 put in the space defined between the flat surface member and the covering.

The covering material may be made of a high-molecular weight material which is impermeable to liquid, flexible and is capable of springing back to its original position even if deformed. For example, a material mainly composed of crosslinked polyethylene foam may be used. This foam may be formed by any known method. Thanks to the use of such resilient material the covering 3 is effective to keep the bicycle saddle shape from deforming which otherwise, would be caused by pressure from the body. Thus, the device can be applied to the body, and be used without deformation.

As the device can hold its shape in use, the device is assured to be in a position in which it may permit the absorbent material to absorb excretion to its full extent, and be soft and comfortable to the body. Also, the covering of crosslinked polyethylene foam is effective to lessen the shock against the urinary organ. The material is not thermally conductive, and in some instances this characteristic may be useful.

A material mainly composed of crosslinked polyolefin, particularly crosslinked polyethylene foam may be used for the covering 3. Such material may have different physical characteristics and sizes. For instance, crosslinked polyethylene foam is formed into a sheet with a thickness range of from 0.5 mm to 5 mm. The extent of foaming ranges from 10 to 40 and apparent density ranges from 0.025 to 0.1. Crosslinked polyolefin is light, and is capable of holding its shape. The material, however, will lose its shape-holding capability if its thickness is below 0.5 mm, and it will have poor flexibility and workability above a certain thickness. It will have poor flexibility and shape-holding capability at an increased degree of foaming. It, however, will have a disadvantageously increased flexibility at a decreased degree of forming, and such material does not expand easily and therefore it is liable to be uncomfortable to wear. A material mainly composed of crosslinked polypropylene foam (crosslinked polyolefin) may also be used. Crosslinked material may be equally used whether the crosslinking is effected by chemical process or electronic process. As for the absorbent material paper, ground pulp, high-molecular weight absorbent material, absorbent wadding and the like, and mixture thereof may be used.

In this particular embodiment, a single sheet forms surface member 2. The part of surface member 2 which contacts the urinary organ, and hence the urine passed from the body, is permeable to liquid, whereas the remaining part of the surface member is not permeable to liquid. The permeable-and-nonpermeable pattern is effective to prevent leakage of excretion from the rear part of the device for the collection of bodily excretion "A" attached to the body in position. Alternatively, the whole area of the surface sheet may be permeable to liquid.

Figure 1:
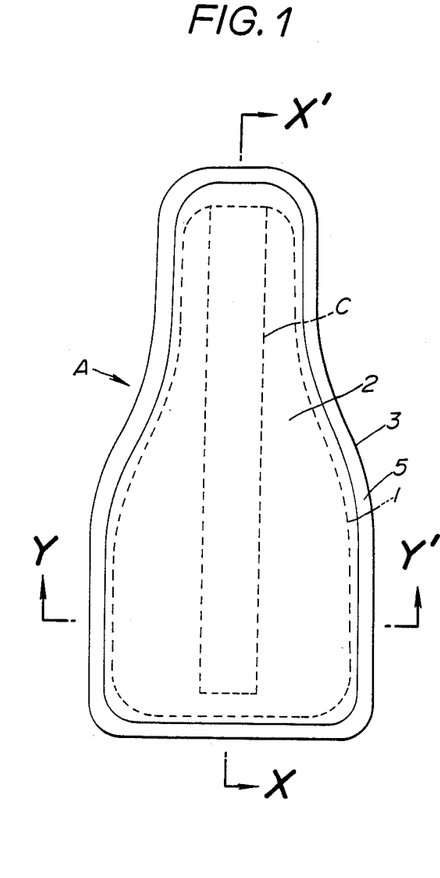
FIG. 1 is a top plane view of the device for collection of bodily excretion according to a first embodiment of the present invention.
Figure 2:
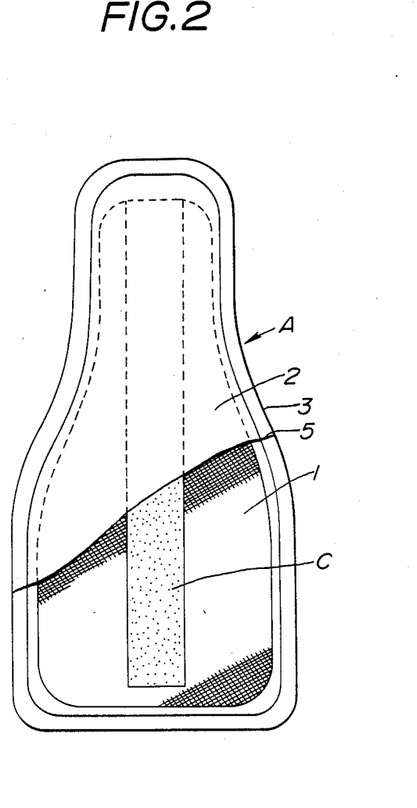
FIG. 2 is a similar plane view, partly broken to show the inside structure of the device.
Figure 3:
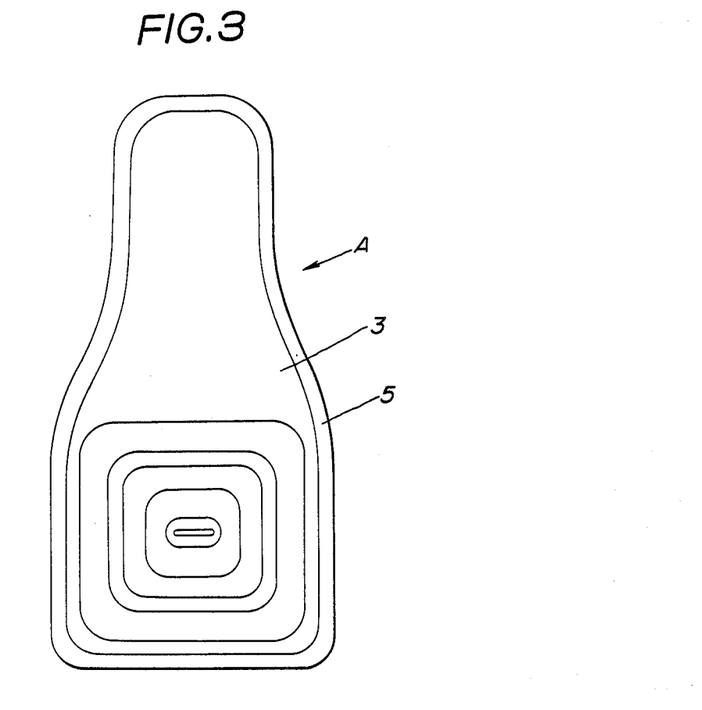
FIG. 3 is a bottom plane view of the device for collection of bodily excretion.
Figure 4:
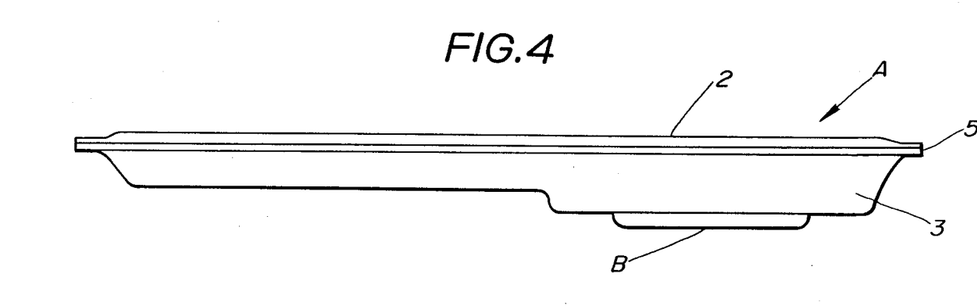
FIG. 4 is a side view of the device for the collection of bodily excretion.
Figure 5:
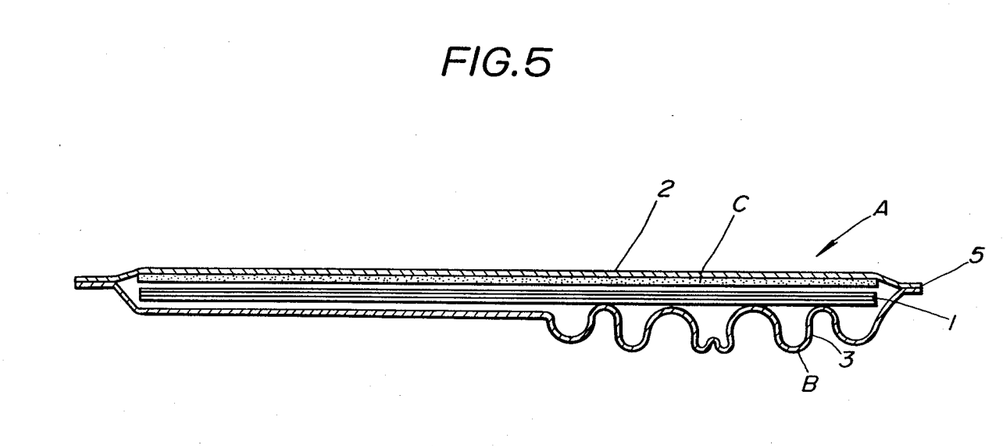
FIG. 5 is a sectional view of the device taken along the line X—X' in FIG. 1.
Figure 6:
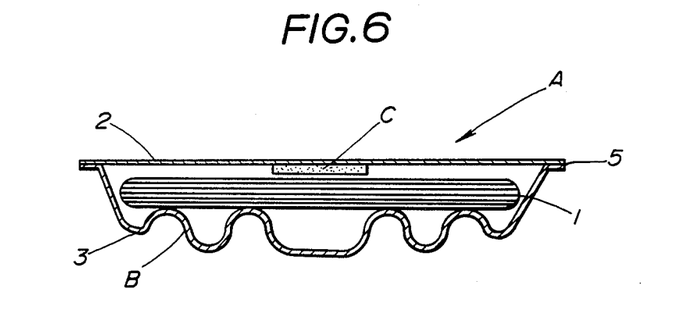
FIG. 6 is a sectional view of the device taken along the line Y—Y' in FIG. 1.
Figure 7:
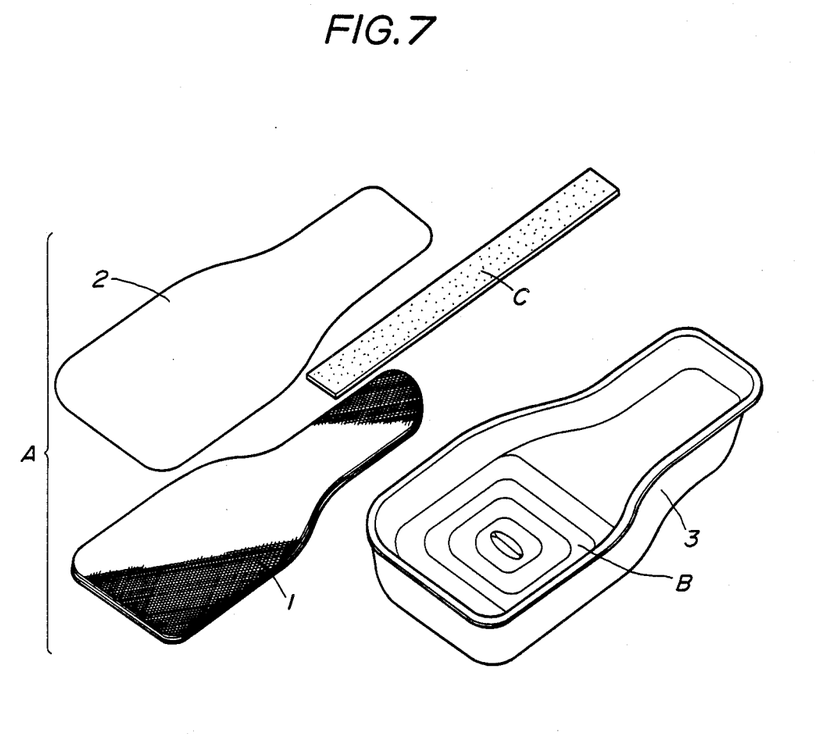
FIG. 7 is an explosive view of the device.
Figure 8:
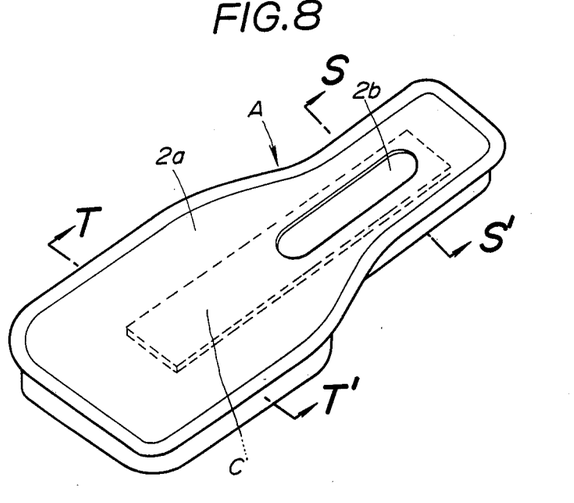
FIG. 8 is a perspective view of device for the collection of bodily excretion according to a second embodiment of the present invention.
Figure 9:
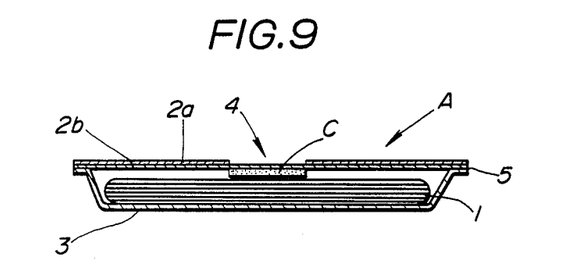
FIG. 9 is a sectional view of the device for the collection of bodily excretion taken along the lines S—S' in FIG. 8.
Figure 10:
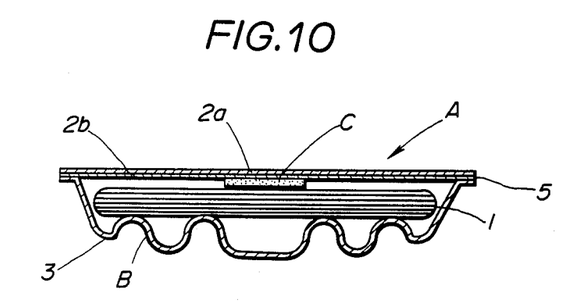
FIG. 10 is a sectional view of the device taken along the line T—T' in FIG. 8.
Figure 11:
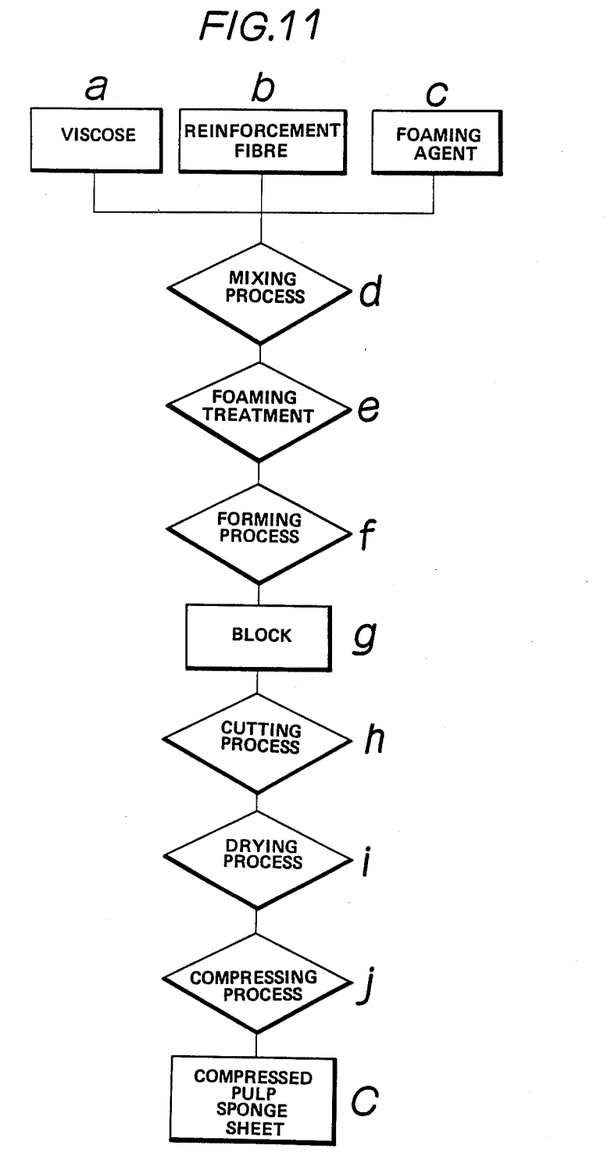
FIG. 11 is a flow chart showing subsequent steps in preparing pulp sponge material, which is used in making a guide strip.

In a second embodiment as shown in FIG. 8 a composite surface member composed of liquid-permeable and impermeable sheets may be used. In this embodiment the front surface layer 2a is of impermeable material, and has a longitudinal slot 4 at its convergent end, which will be put in contact with the urinary organ. On the other hand, the back surface layer 2b is of liquid permeable material. This double-layer structure is also effective to prevent leakage of waste liquid passed from the body.

The device for the collection of bodily excretion "A" according to the present invention has a expandable storage "B" integrally connected to the rear part of the covering 3. The expandable storage "B" is in the form of bellows, which are capable of increasing their volume with the increase of the urine. Prior to excretion, the expandable storage "B" takes its possible minimum volume, somewhat projecting from the flat surface member. In the embodiment shown in the drawings the expandable storage "B" takes a generally square shape.

Figure 12:
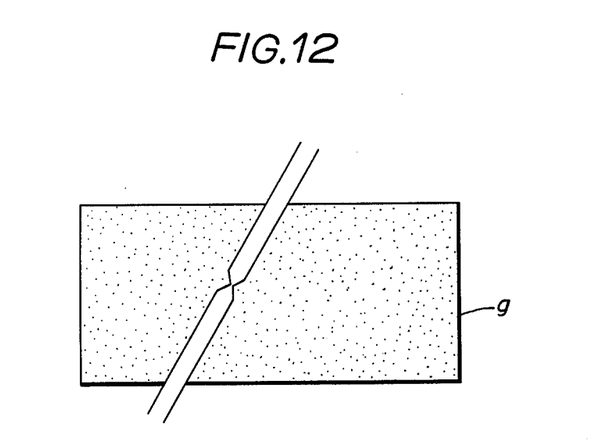
FIG. 12 shows a rectangular mass of pulp sponge material.
Figure 13:
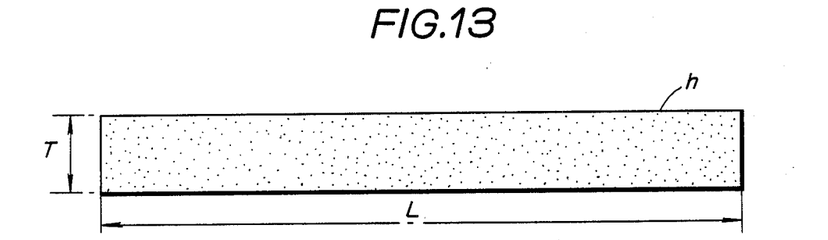
FIG. 13 shows a slice of pulp sponge material.
Figure 14:
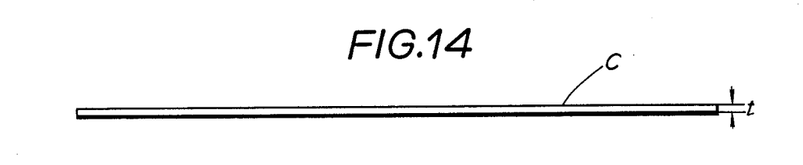
FIG. 14 shows a compressed pulp sponge slice.

A longitudinal guide strip "C" is applied to the absorbent material 1. A pulp sponge material is compressed to a thin sheet, and it is used as guide strip "C". Such pulp sponge material may be prepared by mixing viscose, reinforcement fibre and bubble-forming crystal together, solidifying the mixture, and compressing the resultant sponge material into a sheet. The guide strip "C" is put on the absorbent material 1 along the longitudinal center line of the absorbent material, and the surface member 2 is laid on the guide strip "C". The guide strip "C" extends from the urinary organ-opposing part of the bellows "B". The compressed pulp sponge sheet may be made by any known method. One example of a method of making a compressed pulp sponge sheet is given generally in FIGS. 11 to 14. Viscose "a", foaming agent "c" and reinforcement fibre "b" are mixed together at predetermined ratios. The resultant mixture "d" is subjected to a foaming treatment at Step "e", and then the foamed material is formed into a block at Steps "f" and "g". FIG. 12 shows a sponge block. The rectangular mass of the pulp sponge material is cut to a slice "h" of predetermined length "L" and thickness "T". Then, the sliced sponge is dried at Step "i", and it is compressed into a sheet at Step "j". Thus, a guide strip sheet results. The "t" to "T" compression ratio may be selected at a desired value. When the sliced sponge is compressed to the thinnest possible sheet, it can expand at a maximum ratio in absorbing the urine, "W", thereby enabling itself to transport to the bellows urine of relatively large amounts, compared with the pre-absorption size of the guide strip. In the embodiments as shown in the drawings, the guide strip "C" is put on the absorbent material without being wrapped. It may be wrapped by paper or cotton, and the wrapped guide strip "C" may be fixed to the absorbent material 1 by an adhesive agent, which must be appropriate for sanitary and medical use.

Since the compressed pulp sponge has narrower capillary radii than that of its original sponge, it is capable of absorbing liquid faster. Once wet, it expands and recovers to its original sponge in dimension. When the compressed pulp sponge is only partially wet, the interface between the wet part and the dry part provides a junction area of the unexpanded part having narrow capillaries and the expanded part having wider capillaries or pores. The narrow capillaries draw liquid from the wide ones. Therefore, liquid diffuses from the wet part to the dry part in the compressed pulp sponge strip at a high rate.

Figures 15, 16:
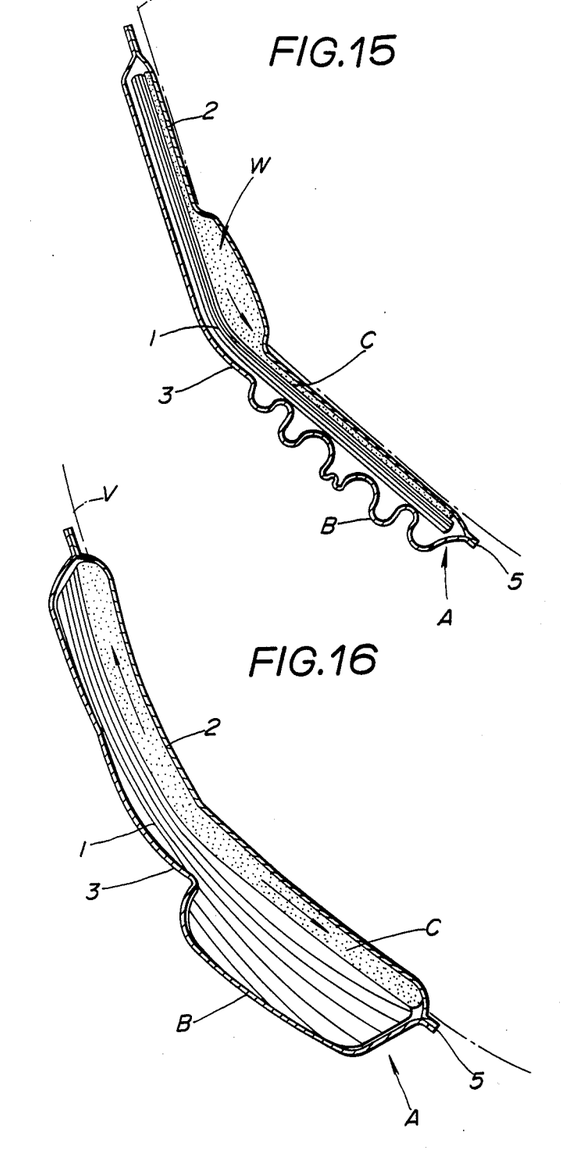
FIG. 15 shows, in section, the manner in which the device for the collection of bodily excretion is applied to the body.
FIG. 16 is a similar view, but showing the position in which the device absorbs and holds the waste liquid passed from the body.

Referring to FIGS. 15 and 16, the manner in which the device for the collection of bodily excretion is used, is described as follows.

FIG. 15 shows the state in which the guide strip "C" begins absorption, whereas FIG. 16 shows the state in which the urine is absorbed and stored.

The device for the collection of bodily excretion "A" is applied to the body with its front or slotted part pushed against the urinary organ "V". The covering 3 keeps the whole device fit onto the bodily, thereby causing a pleasant touch to the body. When the urine "W" is discharged from the body it passes through the flat surface member and is absorbed in the guide strip "C". Specifically, in the embodiment of FIG. 8, the urine "W" passes through the longitudinal slot 4 of the flat surface member 2, not making the surrounding liquid impermeable part wet with urine, "W" and hence not causing any uncomfortable or unpleasant feeling to the body. The guide strip "C" soaks up the urine quickly and accordingly returns to its stress-free, maximum volume. Then, while being absorbed, the urine travels along the guide strip "C" towards the expandable storage at an increased speed. The guide strip material is quick to absorb the urine "W" as it expands towards it initial, stress-free volume, and at the same time, the urine "W" is drawn by capillary influence in the foamed structure of the guide strip "C" material. A relatively large amount of urine "W" will be soaked up when the guide strip expands up to its maximum volume.

The amount of urine "W" to be absorbed in the guide strip "C" depends on the degree of compression of the spongy material. Any extra amount of urine which cannot be absorbed in the guide strip "C" will be gradually soaked up by the underlying absorbent material 1. Such gradual absorption of urine "W" by the absorbent material makes full use of the whole mass of absorbent material, and hence prevents leakage of urine "W" which otherwise, would be caused before the whole volume of absorbent material has been saturated with urine "W".

The surface skin of the guide strip "C" will not be dissolved, and the guide strip "C" will dry quickly because of body temperature When the guide strip "C" dries up, it cannot be in the state of being compressed, but it can absorb the urine "W" well, and then it can direct the flow of urine "W" towards the storage at the rear end of the device for the collection of bodily excretion. The absorption and guiding of urine "W" by the reused guide strip "C" is caused by the capillary effect in the spongy structure of guide strip "C". Reusableness of guide strip "C" permits extended use of the device for the collection of bodily excretion of the present invention. The pulp sponge of the guide strip 20 is mainly made of natural fiber material, causing no adverse effect to the skin. The material easily dries substantially reducing the possibility of collecting bacteria, and removing the need to disinfect bacteria on the material.

The guide strip "C" is in the form of a sheet, and therefore it causes no unpleasant touch to the body. It is easy to manufacture, and is appropriate for disposal and destruction by fire, thereby causing no nuisance.

When the absorbent material 1 is saturated with urine, the expandable storage starts expanding to hold an extra amount of urine. Enlargement of the bellows to their maximum volume completely eliminates the possibility of leakage of urine and/or back-and-overflow from the longitudinal slot 4. Prior to excretion, the expandable storage takes its minimum size, thereby causing no hindrance. At the time of excretion it increases to maximum and is thereby free of leakage or overflow of excretion no matter how much excretion may be discharged.

The device for the collection of bodily excretion according to the preferred embodiment was described as absorbing and holding urine, but it should be understood that the device can be equally used for collecting urine and faeces and monthly bleeding by modifying the device appropriately for the purpose. For instance the expandable storage may be made larger if it is designed for collecting urine and faeces, and the whole size of the device can be reduced for use in absorbing monthly bleeding only.

As may be understood from the above, an excretion absorbing-and-holding device according to the present invention has the following advantages: (1) It has a flat and thin configuration and a small size thereby assuring that the device fits the crotch, thereby not causing an unpleasant touch to the crotch. (2) The device can vary its volume with the amount of excretion, thereby preventing leakage of excretion no matter how much may be discharged. (3) Waste liquid passed from the body can be quickly collected before spreading over an undesired area because of the use of the longitudinal guide strip of compressed mass of pulp sponge material. (4) Waste liquid passed from the body can be quickly transported to the absorbent material and the storage bellows. (5) Excretion can be absorbed and stored at an increased amount per unit volume. (6) Quick absorption and subsequent transportation of excretion is assured without localizing absorption in the absorbent material. (7) Excretion can be repeatedly absorbed and stored. (8) The device can be made easily, and its size and thickness can be reduced to a minimum. (9) The device is appropriate for being thrown away after a single use. (10) Sanitary condition is assured, and (11) the device is soft against the body.

The device of the present invention may be applied to the body by any known method of applying diapers such as adhesive strips or pins.

What is claimed is:

1. A device, adapted to fit on a body for the collection of bodily excretion comprising:

a flexible covering member having a front surface and a rear surface and being formed of a liquid-impermeable material;

a flat surface member shaped so as to be disposed on the front surface of said flexible covering member, said flat surface member and said covering member being hermetically sealed together along their respective peripheries so as to form a shell with a space therebetween;

a liquid absorbent mass disposed in the space between said flat surface member and said flexible covering member; and a storage member disposed integral with the rear surface of said flexible covering member, said storage member having a surface configuration with a concentric undulating form which permits expansion and enlargement of the volume between said flexible covering member and said flat surface member to contain the bodily excretion.

2. A device for the collection of bodily excretion as in claim 1 wherein the flexible covering member is formed of cross-linked polyethylene foam.

3. A device for the collection of bodily excretion as in claim 1 wherein the flexible covering member is formed of cross-linked polypropylene.

4. A device for the collection of bodily excretion as in claim 1 wherein the covering member has a thickness of approximately 0.5 mm to 5 mm.

5. A device for the collection of bodily excretion as in claim 1 wherein the covering member has a bicycle-saddle shape.

6. A device for the collection of bodily excretion as in claim 1 wherein the flat surface member is a sheet of liquid-permeable material.

7. A device for the collection of bodily excretion as in claim 1 wherein the flat surface member is formed of a single composite sheet having a first part formed of a liquid-permeable material and a second part formed of a liquid-impermeable material, said first part being adapted to face a urinary organ when said device is being worn and the second part being adapted to surround said first part.

8. A device according to claim 7, further comprising;

a guide strip disposed in said liquid absorbent mass for absorbing and directing the bodily excretion to flow toward said storage member, said guide strip being adapted to expand its original volume to absorb the bodily excretion and said guide strip extending from said first part of said of said flat surface member to said storage member in order to direct bodily excretions into said storage member.

9. A device for the collection of bodily excretion as in claim 1 wherein the flat surface member is comprised of a double-layer sheet having an overlying liquid-impermeable layer and an underlying liquid-impermeable layer, said overlying layer having a slot which faces a urinary organ when said device is being worn.

10. A device for the collection of bodily excretion as in claim 1 further comprising:

a guide strip disposed in said liquid absorbent mass so as to absorb and direct the bodily excretion to flow toward said storage member, said guide strip being adapted to expand its original volume to absorb the bodily excretion and return to its original volume after the bodily excretion has been directed to said storage member.

* * * * *